United States Patent [19]

Cormier

[11] Patent Number: 4,470,995
[45] Date of Patent: Sep. 11, 1984

[54] USE OF 9-ANTHROYLCHOLINE AS A VAGINAL CONTRACEPTIVE

[75] Inventor: Milton J. Cormier, Bogart, Ga.

[73] Assignee: University of Georgia Research Foundation, Inc., Athens, Ga.

[21] Appl. No.: 545,916

[22] Filed: Oct. 27, 1983

Related U.S. Application Data

[60] Division of Ser. No. 398,848, Jul. 14, 1982, Pat. No. 4,444,789, which is a continuation-in-part of Ser. No. 155,800, May 30, 1980, Pat. No. 4,443,446.

[51] Int. Cl.³ .......................................... A61K 31/235
[52] U.S. Cl. ............................ 424/308; 424/DIG. 14
[58] Field of Search ........................ 424/308, DIG. 14

[56] References Cited

U.S. PATENT DOCUMENTS 3,873,583  3/1975  Walz et al. .......................... 260/404
4,443,446  4/1984  Cormier .............................. 424/247
4,444,789  4/1984  Cormier .............................. 424/315

Primary Examiner—Leonard Schenkman
Attorney, Agent, or Firm—Sumner C. Rosenberg

[57] ABSTRACT

The use of 9-anthroylcholine as a vaginal contraceptive is disclosed. The invention may be implemented by incorporating the drug in a known method such as jelly, foam, or suppository introduction means prior to intercourse.

8 Claims, No Drawings

USE OF 9-ANTHROYLCHOLINE AS A VAGINAL CONTRACEPTIVE

This is a division of application Ser. No. 398,848, filed July 14, 1982 now U.S. Pat. No. 4,444,789 which is a continuation-in-part of application Ser. No. 155,800, filed May 30, 1980 now U.S. Pat. No. 4,443,446.

The present invention relates to a method of preventing conception. More specifically, the present invention relates to the use of calmodulin binding drugs as vaginal contraceptives.

Presently, many forms of contraception are available, including oral contraceptives, mechanical contraceptives, and vaginal contraceptive solutions generally comprising spermatocides. Each form of contraception suffers from undesirable characteristics such as varying effectiveness, discomfort, or physical side effects.

Vaginal contraceptives comprising spermatocidal agents are well known in the prior art in many methods of usage, including jellies and creams (hereinafter referred to as jelly), foams from tablets or aerosols, and suppositories. However, these methods are among the least effective in terms of preventing conception and are basically unsatisfactory as a sole method of contraception.

DESCRIPTION OF THE INVENTION

The present invention comprises the use of certain calmodulin binding drugs as vaginal contraceptives. The introduction of such drugs into the vagina can be accomplished by any of the many commonly available methods currently used in conjunction with spermatocides, such as jelly, foam or suppository means. By substitution of the appropriate amount or concentration of an effective calmodulin binding drug in place of, or in addition to, the spermatocidal agent in any of these means, a form of contraceptive embodying the invention, to be applied in the same manner prior to sexual intercourse, is accomplished.

As stated previously, current forms of vaginal contraceptives are based on the use of spermatocides, which are intended to kill the sperm. Generally, the use of such contraceptives by themselves have not proven to be a satisfactorily effective contraceptive method. The present invention does not involve the killing of the sperm, but instead directly and specifically blocks the physiological process of conception and results in greatly improved effectiveness of contraception.

It has been shown in the past years that there is a regulatory protein known as calmodulin, found in all cells of higher organisms and which is the key to the control of a wide variety of physiological processes. We have found that calmodulin is involved in triggering the activation of mammalian spermatozoa, a prerequisite to the fertilization process. Calmodulin is a calcium binding protein, which means that when calcium is bound to the protein the resulting calcium-protein complex turns on a variety of cellular processes including spermatozoan activation.

Calmodulin binding drugs are drugs that will bind tightly to calmodulin only in the presence of calcium. The binding of these drugs to calmodulin results in the inhibition of calmodulin function.

The use of an effective calmodulin binding drug as a vaginal contraceptive has a number of advantages. First, it is extremely effective since the specific binding of the drug to calmodulin would turn off spermatozoan activation and thus prevent fertilization. Experimental evidence has demonstrated that the phenothiazine drugs penetrate the spermatozoan membranes within seconds and concentrate in the region of the cell occupied by calmodulin. Second, there will be no expected side effects since the drug would not be used internally and since low concentrations will be very effective as a vaginal contraceptive. Third, the effectiveness of an application may last for hours due to the stability of these drugs.

Additionally, evidence has indicated that calmodulin is also the target protein during ovum activation since this is also a calcium dependent process. Thus if the drug comes into contact with the ovum, fertilization will not occur. It is seen, therefore, that the present invention may be doubly effective by preventing activation of both the sperm and the egg.

The most effective drugs for contraceptive purposes can be predicted based on their effectiveness in binding to calmodulin. The following calmodulin binding drugs have been found to be effective as contraceptives:

1. penfluridol,
2. pimozide,
3. trifluoperazine,
4. chlorprothixene,
5. thioridazine,
6. chlorpromazine,
7. benperidol,
8. haloperidol,
9. clozapine,
10. 8-anilino-1-naphthalenesulfonate,
11. 9-anthroylcholine,
12. N-phenyl-1-naphthylamine,
13. N-(6 aminohexyl)-5-chloro-1-naphthalenesulfonamide,
14. N-(6 aminohexyl)-5-chloro-2-naphthalenesulfonamide,
15. N-(6 aminohexyl)-5-bromo-2-naphthalenesulfonamide,
16. Phenothiazine sulfoxide,
17. Chlorpramazine sulfoxide,
18. 2-Trifluromethyl-N-10 (3'-proprioamino) phenothiazine sulfoxide.

While a concentration of 0.5% (5 milligrams per milliliter of jelly) will be effective in the most effective drugs such as penfluridol or chlorpramazine sulfoxide, less effective drugs will require a higher concentration to achieve similar effectiveness. Introduction of about 10 milligrams of 9-anthroylcholine into the vagina is desirable for effectiveness.

An embodiment of the present invention comprises a one-half percent concentration of 9-anthroylcholine in a jelly, introduced into the vagina in sufficient quantity and under known methods prior to sexual intercourse and allowed to remain therein for a period of time, preferably more than a few hours, after intercourse.

What is claimed is:

1. A method of preventing conception in a female which comprises: introducing an effective amount of the drug 9-anthroylcholine into the vagina of the female.

2. The method as described in claim 1, wherein the introduction of said drug comprises the steps of: introducing said drug into the vagina of the female prior to sexual intercourse; and allowing said drug to remain in the vagina during and after sexual intercourse.

3. The method as described in claim 2, wherein the step of introducing said drug comprises introducing a mixture of said drug and a foam carrier into the vagina of the female prior to sexual intercourse by foam injection means.

4. The method as described in claim 2, wherein the step of introducing said drug comprises introducing a mixture of said drug and jelly carrier into the female prior to sexual intercourse by jelly insertion means.

5. The method as described in claim 2, wherein said drug is introduced into the vagina of the female by suppository means.

6. The method as described by claim 3, wherein the amount of the drug introduced into the vagina is about 10 milligrams or greater.

7. The method as described in claim 4, wherein the amount of the drug introduced into the vagina is about 10 milligrams or greater.

8. The method as described in claim 5, wherein the amount of the drug introduced into the vagina is about 10 milligrams or greater.

* * * * *